(12) United States Patent
Son et al.

(10) Patent No.: US 9,044,406 B2
(45) Date of Patent: *Jun. 2, 2015

(54) AQUEOUS COMPOSITION FOR ENTERIC HARD CAPSULE, METHOD OF PREPARING ENTERIC HARD CAPSULE, AND ENTERIC HARD CAPSULE PREPARED USING THE METHOD

(75) Inventors: Jin Ryul Son, Incheon (KR); Hyon Ho Baek, Incheon (KR); Sung Wan Lee, Incheon (KR); Min Gyu Song, Seoul (KR); Jae Uk Cha, Seoul (KR); Eun Hee Park, Incheon (KR)

(73) Assignee: SAMSUNG FINE CHEMICALS CO., LTD. (KR)

( * ) Notice: Subject to any disclaimer, the term of this patent is extended or adjusted under 35 U.S.C. 154(b) by 370 days.

This patent is subject to a terminal disclaimer.

(21) Appl. No.: 13/378,249

(22) PCT Filed: Oct. 13, 2009

(86) PCT No.: PCT/KR2009/005870
§ 371 (c)(1),
(2), (4) Date: Dec. 14, 2011

(87) PCT Pub. No.: WO2011/030952
PCT Pub. Date: Mar. 17, 2011

(65) Prior Publication Data
US 2012/0161364 A1    Jun. 28, 2012

(30) Foreign Application Priority Data
Sep. 11, 2009    (KR) .................. 10-2009-0085876

(51) Int. Cl.
| | | |
|---|---|---|
| B28B 1/38 | (2006.01) | |
| A61K 9/48 | (2006.01) | |
| A61K 47/38 | (2006.01) | |

(52) U.S. Cl.
CPC ............... *A61K 9/4816* (2013.01); *A61K 47/38* (2013.01)

(58) Field of Classification Search
USPC ................................. 264/304–306, 214, 215
See application file for complete search history.

(56) References Cited

U.S. PATENT DOCUMENTS

| | | | |
|---|---|---|---|
| 4,138,013 A | 2/1979 | Okajima | |
| 4,655,840 A | 4/1987 | Wittwer et al. | |
| 2004/0192907 A1* | 9/2004 | Resch et al. | 536/123 |

FOREIGN PATENT DOCUMENTS

| | | |
|---|---|---|
| EP | 0056825 A1 | 8/1982 |
| EP | 2223685 A1 | 9/2010 |
| JP | 1976128421 A | 11/1976 |
| JP | 1982142251 A | 9/1982 |
| JP | 2006-016372 | 1/2006 |
| JP | 2007-230948 | 9/2007 |
| TW | I283586 B | 7/2007 |
| WO | 98/22095 | 5/1998 |
| WO | 00/18377 | 4/2000 |
| WO | 2008050209 A1 | 5/2008 |
| WO | 2009062356 A1 | 5/2009 |

OTHER PUBLICATIONS

European Search Report dated Oct. 24, 2013 of the European Patent Application No. 09849269.7, 7 pages.
JP Office Action dated Nov. 7, 2013 of the Japanese Patent Application No. 2012-528723 with English Translation, 6 pages.
International Search Report—PCT/KR2009/005870 dated Oct. 15, 2010.
Taiwanese Office Action with English Translation for Application No. 098135631 dated Mar. 13, 2013.
Hydroxypropyl Methylcellulose, Aug. 26, 2002, p. 1-2; Retrieved from the internet: URL:http//www.ams.usda.gov/AMSv1.0/getfile?dDocName=STELPRDC5090706.

* cited by examiner

*Primary Examiner* — Stella Yi
(74) *Attorney, Agent, or Firm* — Cantor Colburn LLP

(57) ABSTRACT

An aqueous composition for an enteric hard capsule, a method of preparing an enteric hard capsule, and an enteric hard capsule prepared using the method. The aqueous composition for an enteric hard capsule includes an enteric base material, a capsule forming aid, and a neutralizing agent. The method of preparing an enteric hard capsule includes: preparing an aqueous composition by dissolving an enteric base material, a capsule forming aid, and a neutralizing agent in water; preheating the aqueous composition to a temperature that is less than the gelation temperature for the aqueous composition; immersing a mold pin heated to a temperature that is greater than the gelation temperature for the aqueous composition into the aqueous composition; taking the mold pin out of the aqueous composition to obtain a film formed on the mold pin; and maintaining the film at a temperature that is equal to or greater than the gelation temperature for the aqueous composition for a predetermined period of time to fix the film on the mold pin and drying the film.

1 Claim, No Drawings

AQUEOUS COMPOSITION FOR ENTERIC HARD CAPSULE, METHOD OF PREPARING ENTERIC HARD CAPSULE, AND ENTERIC HARD CAPSULE PREPARED USING THE METHOD

TECHNICAL FIELD

The present invention relates to an aqueous composition for an enteric hard capsule, a method of preparing an enteric hard capsule, and an enteric hard capsule prepared using the method. More particularly, the present invention relates to an aqueous composition for an enteric hard capsule including an enteric base material, a capsule forming aid, and a neutralizing agent, a method of preparing an enteric hard capsule, and an enteric hard capsule prepared using the method.

BACKGROUND ART

Capsules for accommodating pharmaceutical preparations and functional foods are generally prepared using gelatin and hydroxypropyl methylcellulose (HPMC) as base materials.

A gelatin capsule may lead to improved productivity and price competitiveness. However, if the gelatin capsule contains moisture of 10 wt % or less, plasticity and impact resistance thereof may be reduced. In addition, since the use of gelatin is limited due to mad cow disease or the like, an HPMC capsule formed of a plant-based material without using gelatin has been widely used.

In general, methods of preparing hard capsules are classified into two types, freeze-gelation and thermal gelation, according to gelation properties.

A capsule may be prepared using freeze-gelation including: heating a gelatin solution that is gelated at room temperature or a HPMC solution including carrageenan, agar, sodium alginate, gellan gum, and/or pectin which are gelated at room temperature and maintaining the solution at a high temperature to mature the gelatin or the HPMC of the solution; immersing a cold mold pin in the solution and coating the mold pin with a predetermined amount of the solution; and taking the mold pin out of the solution, immediately applying cold air having a temperature of about 20° C. to the mold pin to gelate the gelatin or the HPMC of the solution, and drying the gel. In the freeze-gelation, carrageenan, agar, sodium alginate, gellan gum, pectin, or the like are widely used in the preparation of capsules as a gelating agent since they bind to metal ions such as potassium, calcium, and sodium to increase gelation capability. However, when a capsule including impurities such as carrageenan is orally administered, the impurities react with metal salts in the gastric juice or intestinal juice, so that a binding force among components of the capsule increases, thereby inhibiting disintegration of the capsule.

A capsule may also be prepared using thermal gelation using gelating features of HPMC in an HPMC solution at a high temperature. A high-temperature mold pin is immersed in an HPMC solution maintained at a temperature equal to or greater than room temperature to thermally gelate the HPMC of the HPMC solution coated on the mold pin by the heat of the mold pin.

However, since the capsule is orally administered, disintegrated by gastric juice and absorbed in the body, it may not be used in case that main ingredients and excipients of pharmaceutical preparations and functional foods filled in the capsule are instable in an acid, irritate the stomach, or generate an odor that can be regurgitated. In this case, the surface of the capsule is coated with an enteric base material after filling the capsule, so that the capsule can have enteric properties.

However, for the coating of the capsule with the enteric base material, a process for the coating is further required, and thus the manufacturing costs increase. Furthermore, an organic solvent contained in a coating solution may remain on the surface of the capsule during the coating, an identification code of the capsule may become invisible due to the coating, or the quality of appearance of the capsule may be deteriorated after the coating.

Therefore, much research has been conducted to develop an enteric hard capsule. However, an enteric hard capsule with high quality and high productivity has not been commercialized.

DETAILED DESCRIPTION OF THE INVENTION

Technical Problem

The present invention provides an aqueous composition for an enteric hard capsule including an enteric base material, a capsule forming aid, and a neutralizing agent.

The present invention also provides a method of preparing an enteric hard capsule by using the aqueous composition.

The present invention also provides an enteric hard capsule prepared according to the method.

Technical Solution

According to an aspect of the present invention, there is provided an aqueous composition for an enteric hard capsule including an enteric base material, a capsule forming aid, and a neutralizing agent.

The enteric base material may include at least one compound selected from the group consisting of hydroxypropyl methylcellulose phthalate (HPMCP) and hydroxypropyl methylcellulose acetate succinate (HPMCAS).

The capsule forming aid may include cellulose ether.

The cellulose ether may include at least one compound selected from the group consisting of hydroxypropyl methylcellulose (HPMC) and methylcellulose (MC).

The neutralizing agent may be a basic compound.

The amount of the enteric base material may be in the range of about 8 to about 25% based on the total weight of the aqueous composition.

The amount of the capsule forming aid may be in the range of about 1 to about 12% based on the total weight of the aqueous composition.

The amount of the neutralizing agent may be in the range of about 1 to about 5% based on the total weight of the aqueous composition.

The aqueous composition may further include an emulsifier having an amount of 1.0% or less based on the total weight of the aqueous composition.

The aqueous composition may further include a plasticizer having an amount of 4.0% or less based on the total weight of the aqueous composition.

According to another aspect of the present invention, there is provided a method of preparing an enteric hard capsule, the method including: preparing an aqueous composition by dissolving an enteric base material, a capsule forming aid, and a neutralizing agent in water and maturing the solution at room temperature; preheating the aqueous composition to a first temperature that is less than the gelation temperature for the aqueous composition; immersing a mold pin heated to a second temperature that is greater than the gelation temperature for the aqueous composition into the aqueous composition;

taking the mold pin out of the aqueous composition to obtain a film formed on the mold pin; and preparing a capsule shell by maintaining the film at a third temperature that is equal to or greater than the gelation temperature for the aqueous composition for a first time period to fix the film on the mold pin and drying the film at a fourth temperature for second time period.

The first temperature may be less than the gelation temperature for the aqueous composition by about 4 to about 12.0° C.

The second temperature may be greater than the gelation temperature for the aqueous composition by about 10 to about 31° C.

The third temperature may be in the range of about 60 to about 80° C., and the first time period may be in the range of about 1 to about 15 minutes.

The fourth temperature may be in the range of about 20 to about 40° C., and the second time period may be in the range of about 30 to about 60 minutes.

According to another aspect of the present invention, there is provided an enteric hard capsule prepared according to the method.

DESCRIPTION OF THE DRAWINGS

Hereinafter, an aqueous composition for an enteric hard capsule according to an embodiment of the present invention will now be described in detail.

The aqueous composition for an enteric hard capsule according to the present embodiment includes an enteric base material, a capsule forming aid, and a neutralizing agent. The "aqueous composition" used herein indicates a composition in which at least the enteric base material, the capsule forming aid, and the neutralizing agent are dissolved in water.

The enteric base material that is gelated in an aqueous solution at a high temperature is not dissolved in gastric juice having a pH of about 1.2 for 2 to 4 hours but rapidly dissolved in small intestinal juice having a pH of about 6.8 within about 10 minutes. The enteric base material may include at least one compound selected from the group consisting of hydroxypropyl methylcellulose phthalate (HPMCP) and hydroxypropyl methylcellulose acetate succinate (HPMCAS). The HPMCP may be HPMCP HP-55 (methoxy: 18 to 22%, hydroxypropoxy: 5 to 9%, phthalic acid: 27 to 35%, 200731 Type, viscosity: 32 to 48 cSt), HPMCP HP-55S(methoxy: 18 to 22%, hydroxypropoxy: 5 to 9%, phthalic acid: 27 to 35%, 200731 Type, viscosity: 136 to 204 cSt), and HPMCP HP-50 (methoxy: 20 to 24%, hydroxypropoxy: 6 to 10%, phthalic acid: 21 to 27%, 220824 Type, viscosity: 44 to 66 cSt), which are produced by Samsung Fine Chemicals Co., Ltd. The amounts of methoxy or other substituents refer to ratios of the total atomic weight of elements constituting each of the substituents to the total atomic weight of elements constituting a repeating unit of cellulose as shown in the formula below.

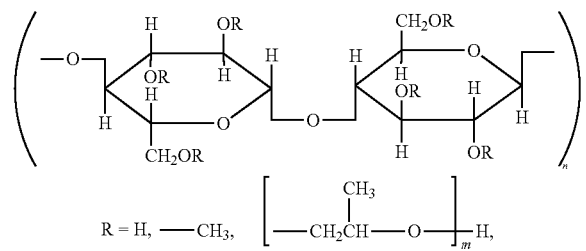

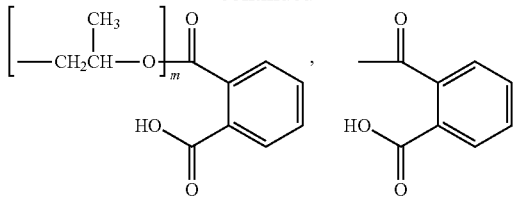

-continued

In the formulae above, m and n are each independently an integer equal to or greater than 1.

The amount of the enteric base material may be in the range of about 8 to about 25%, for example, about 12 to about 21% of the total weight of the aqueous composition. In this regard, the viscosity of the aqueous composition may be in the range of about 1000 to about 3000 cps at room temperature. If the amount of the enteric base material is less than 8% based on the amount of the total weight of the aqueous composition, the viscosity of the aqueous composition is so low that the film thickness of the capsule prepared using the aqueous composition is too thin and the enteric properties of the capsule may be deteriorated. On the other hand, if the amount of the enteric base material is greater than 25% based on the amount of the total weight of the aqueous composition, the viscosity of the aqueous composition is so high that the film thickness of the capsule prepared using the aqueous composition is too thick.

The capsule forming aid that improves elasticity of the fragile film of the enteric capsule to improve capsule formability, and controls the gelation temperature of the aqueous composition in the range of about 20 to about 70° C., may include cellulose ether. The cellulose ether may include at least one compound selected from the group consisting of hydroxypropyl methylcellulose (HPMC) and methylcellulose (MC). The HPMC may include about 4 to about 12%, for example, about 4 to about 7.5%, of hydroxypropoxy and about 19 to about 30%, for example, about 27 to about 30%, of methoxy. In addition, the viscosity of 2 wt % HPMC aqueous solution may be in the range of about 3 to about 50 cps, for example, about 3 to about 15 cps. In addition, the amount of the capsule forming aid may be in the range of about 1 to about 12%, for example, about 3 to about 10% based on the total weight of the aqueous composition. If the amount of the capsule forming aid is less than 1% based on the total weight of the aqueous composition, elasticity of the capsule may decrease. On the other hand, if the amount of the capsule forming aid is greater than 12%, enteric properties of the capsule may be deteriorated.

The neutralizing agent that solubilizes the enteric base material may be a basic material such as sodium hydroxide, aqueous ammonia, potassium hydroxide, and calcium hydroxide. In addition, the neutralizing agent may decrease the gelation temperature according to types of salts. The amount of the neutralizing agent may be in the range of about 1 to about 5%, for example, about 2 to about 4% based on the total weight of the aqueous composition. If the amount of the neutralizing agent is less than 1% based on the total weight of the aqueous composition, it is difficult to solubilize the enteric base material. On the other hand, if the amount of the neutralizing agent is greater than 5%, the solubilization may be quickly conducted, but the aqueous composition may exhibit strong basic properties or the enteric properties may be deteriorated.

The aqueous composition may further include an emulsifier to improve capsule formability. The emulsifier may be sodium lauryl sulfate (SLS), sucrose esters of fatty acids, and a mixture thereof. In particular, the SLS has excellent capsule formability. The amount of the emulsifier may be in the range of about 0.01 to about 1.0%, for example, about 0.05 to about 0.5% based on the total weight of the aqueous composition. If the amount of the emulsifier is less than 0.01% based on the total weight of the aqueous composition, capsule formability may be deteriorated since the solution coated on a mold pin is rolled up. On the other hand, if the amount of the emulsifier is greater than 1.0% based on the total weight of the aqueous composition, the capsule may have poor quality and low safety, for example, thereby causing gastroenteric trouble.

The aqueous composition may further include a plasticizer to improve the film strength of the capsule. The plasticizer may include at least one compound selected from the group consisting of diacetylated monoglyceride, triethyl citrate (TEC), triacetin (TA), polyethylene glycol (PEG), and propylene glycol (PG). In particular, diacetylated monoglyceride has excellent acid resistance. In addition, the amount of the plasticizer may be in the range of about 0.1 to about 4.0%, for example, about 0.2 to about 2.0% based on the total weight of the aqueous composition. If the amount of the plasticizer is less than 0.1% based on the total weight of the aqueous composition, the film of the capsule may not have plasticity. On the other hand, if the amount of the plasticizer is greater than 4.0%, plasticity of the capsule increases, but transparency of the capsule decreases.

The aqueous composition may be prepared according to the following method.

That is, an aqueous composition may be prepared by: preparing an aqueous solution by dissolving additives such as a neutralizing agent and, selectively, an emulsifier and a plasticizer in water, and adding an enteric base material and a capsule forming aid to the aqueous solution and dissolving them.

Hereinafter, a method of preparing an enteric hard capsule by using the aqueous composition will be described.

The method of preparing the enteric hard capsule according to an embodiment of the present invention includes the following operations:

(1) preparing an aqueous composition by dissolving an enteric base material, a capsule forming aid, and a neutralizing agent in water. The aqueous composition may have a pH ranging from about 4.5 to about 6.5 and a viscosity ranging from about 1000 to about 3000 cps, for example, about 1500 to about 2500 cps at room temperature. Even though the enteric base material is thermally gelated at about 75° C., the gelation temperature for the aqueous composition may vary according to the ratio between the enteric base material and the capsule forming aid, and may be controlled to a temperature ranging from about 50 to about 60° C. In addition, the aqueous composition may further include titanium dioxide and/or colorants such as mineral colorants, natural colorants, and tar colorants;

(2) preheating the aqueous composition to a first temperature that is less than the gelation temperature for the aqueous composition;

(3) immersing a mold pin heated to a second temperature that is greater than the gelation temperature for the aqueous composition into the aqueous composition.

(4) taking the mold pin out of the aqueous composition to obtain a film formed on the mold pin;

(5) preparing a capsule shell by maintaining the film at a third temperature that is equal to or greater than the gelation temperature for the aqueous composition for a first time period to fix the film on the mold pin and drying the film at a fourth temperature for a second time period.

Specifically, the method of the enteric hard capsule is characterized by 3 major factors. The first factor is the temperature of the aqueous composition. The temperature of the aqueous composition determines the fluidity of the aqueous composition coated on the mold pin. The aqueous composition may be maintained at a temperature (first temperature) that is less than the gelation temperature therefor by about 4 to about 12° C., for example, about 5 to about 10° C. If the first temperature is less than the gelation temperature for the aqueous composition by less than 4° C., the fluidity of the aqueous composition is reduced since the aqueous composition is fixed as soon as the mold pin is taken out of the aqueous composition, so that an appropriate film may not be obtained. On the other hand, if the first temperature is less than the gelation temperature of the aqueous composition by greater than 12° C., it is difficult to form the capsule due to too high fluidity. The second factor is the temperature of the mold pin. The temperature of the preheated mold pin is an important factor to determine the film thickness of the capsule. The film thickness of the capsule may decrease as the temperature decreases, and the film thickness of the capsule may increase as the temperature increases. The mold pin may be maintained at a temperature (second temperature) that is greater than the gelation temperature for the aqueous composition by about 10 to about 31° C. even though the temperature of the mold pin may vary according to the size of the capsule. If the second temperature is greater than the gelation temperature for the aqueous composition by less than 10° C., the film thickness of the capsule is too thin. On the other hand, if the second temperature is greater than the gelation temperature of the aqueous composition by greater than 31° C., the film thickness of the capsule is too thick. The third factor is the drying temperature. The drying temperature generally controls the fluidity of the aqueous composition coated on the mold pin. In general, the aqueous composition coated on the mold pin is transferred to a drying device to be dried. In this regard, in the beginning of the drying, the aqueous composition is maintained at a temperature (third temperature) that is equal to or greater than the gelation temperature for the aqueous composition for a predetermined period of time (first time period) to completely fix the aqueous composition on the mold pin to prevent the aqueous composition from flowing. The third temperature may be in the range of about 60 to about 80° C., and the first time period may be in the range of about 1 to about 15 minutes, for example, about 3 minutes. If the third temperature is less than 60° C. or the first time period is less than 1 minute, the coated aqueous composition cannot be fixed on the mold pin, but flows, so that the capsule cannot be formed. On the other hand, if the third temperature is greater than 80° C. or the first time period is greater than 15 minutes, the aqueous composition is over-dried, so that moisture of the film of the capsule is rapidly reduced to cause cracks on the capsule. Then, the mold pin is maintained in a drying device at the fourth temperature for a second time period to completely dry the capsule. The fourth temperature may be in the range of about 20 to about 40° C., and the second time period may be in the range of about 30 to about 60 minutes. If the fourth temperature is less than 20° C. or the second time period is less than 30 minutes, the coated aqueous composition has so much moisture that the capsule may be easily deformed. On the other hand, if the fourth temperature is greater than 40° C. or the second time period is greater than 60 minutes, the coated aqueous composition is over dried to have low moisture, so that the strength of the capsule may decrease to cause cracks.

By combining the three factors, the enteric hard capsule with excellent quality similar to that of currently commercially available capsules may be prepared. The enteric hard capsule prepared according to the method described above may be applied to various uses, for example, pharmaceutical preparations and functional foods.

Hereinafter, one or more embodiments will be described in detail with reference to the following examples. However, these examples are not intended to limit the purpose and scope of the invention.

EXAMPLES

Examples 1 to 16

Aqueous compositions having compositions listed in Table 1 below were prepared according to the following method, and enteric capsules were prepared in the conditions listed in Table 2 below. Then, each of the prepared capsules was immersed in a test solution having the pH of 1.2 that is similar to gastric juice for maximum 2 hours to observe whether it disintegrate or not, and then immersed in a test solution having the pH of 6.8 that is similar to small intestinal juice to measure disintegration time.

The results are shown in Table 2 below.

Preparation of Aqueous Composition

A neutralizing agent, an emulsifier, and a plasticizer, and selectively, a colorant were added to water, and an enteric base material and a capsule forming aid were added thereto and dissolved therein to prepare aqueous compositions.

Preparation of Enteric Capsule

The temperature of each of the aqueous compositions prepared as described above was controlled to be less than a thermal gelation temperature for the aqueous compositions by 4 to 12° C. Then, a mold pin (Technophar Equipment & Service Ltd., pin, #0) preheated to a temperature that is greater than the thermal gelation temperature for the corresponding aqueous composition by 10 to 31° C. was immersed in the aqueous composition to coat the aqueous composition on the mold pin. Then, the coated aqueous composition was gelated. The mold pin coated with the aqueous composition was maintained at a temperature ranging from 60 to 80° C. for 3 minutes and dried at a temperature ranging from 20 to 40° C. for 30 to 60 minutes.

TABLE 1

Composition of aqueous composition (wt %)[*1]

| Example | enteric base material | | capsule forming acid | | | | Neutralizing agent | | | | Emulsifier | Plasticizer | | Colorant |
|---|---|---|---|---|---|---|---|---|---|---|---|---|---|---|
| | HPMCP[*2] | HPMCAS[*3] | MC[*4] | HPMC 2910[*5] | HPMC 2208[*6] | HPMC 2906[*7] | NaOH | NH4OH | KOH | Ca(OH)2 | SLS | TEC | Mivacet[*8] | TiO2 |
| 1 | 17.36 | — | — | — | — | 4.34 | 1.39 | — | — | — | — | — | — | — |
| 2 | 20.21 | — | — | — | — | 2.25 | 1.60 | — | — | — | 0.02 | 0.02 | — | 2.53 |
| 3 | 17.41 | — | — | — | — | 4.35 | 1.39 | — | — | — | 0.02 | 0.02 | — | — |
| 4 | 17.35 | — | — | 4.34 | — | — | 1.39 | — | — | — | 0.02 | 0.02 | — | — |
| 5 | 14.13 | — | — | 7.61 | — | — | 1.13 | — | — | — | 0.02 | 0.02 | — | — |
| 6 | 18.42 | — | — | — | — | 3.25 | — | 1.48 | — | — | 0.02 | 0.02 | — | — |
| 7 | 17.35 | — | — | — | — | 4.34 | — | 1.81 | — | — | 0.05 | — | 0.05 | — |
| 8 | 13.84 | — | — | — | — | 5.93 | — | 1.65 | — | — | 0.02 | 0.02 | — | — |
| 9 | 17.35 | — | 4.34 | — | — | — | 1.39 | — | — | — | 0.02 | 0.02 | — | — |
| 10 | 17.35 | — | — | — | — | 4.34 | 1.39 | — | — | — | 0.02 | 0.02 | — | — |
| 11 | 17.20 | — | — | — | — | 4.30 | — | — | 2.24 | — | — | — | — | — |
| 12 | 17.16 | — | — | — | — | 4.29 | 1.39 | — | — | 0.21 | — | — | — | — |
| 13 | — | 15.24 | — | — | — | 6.54 | — | 0.92 | — | — | 0.02 | 0.02 | — | — |
| 14 | 15.21 | — | — | — | 6.52 | — | 1.22 | — | — | — | 0.02 | 0.02 | — | — |
| 15 | 17.32 | — | — | — | — | 4.33 | 1.39 | — | — | — | 0.20 | 0.02 | — | — |
| 16 | 17.18 | — | — | — | — | 4.30 | 1.37 | — | — | — | 0.02 | 1.00 | — | — |

[*1]: The remaining weight percent of water was added to the aqueous composition.
[*2]: HPMCP HP-55, produced by Samsung Fine Chemicals, Co., Ltd.
[*3]: HPMCAS AS-LF, produced by Shin-Etsu Chemical Co., Ltd.
[*4]: MC having a viscosity of 8 cps, produced by Samsung Fine Chemicals, Co., Ltd.
[*5]: AnyCoat-C AN4, produced by Samsung Fine Chemicals, Co., Ltd.
[*6]: AnyCoat-C CN4, produced by Samsung Fine Chemicals, Co., Ltd.
[*7]: AnyCoat-C BN4, produced by Samsung Fine Chemicals, Co., Ltd.
[*8]: Mivacet 9-45K food grade, produced by Esterol Sdn.Bhd.(Malaysia)

TABLE 2

| | Conditions for forming capsule[*1] | | | Performance of capsule | | | | |
|---|---|---|---|---|---|---|---|---|
| | Gelation | Temperature of aqueous | Temperature of mold pin | Shape of capsule[*2] | | | Disintegration time (min) | |
| Example | temperature (° C.) | composition (° C.) | (° C.) | Transparency | Gelation force | Elasticity of film | pH 1.2 | pH 6.8 |
| 1 | 57 | 48 | 73 | ◎ | ◎ | ◎ | >120 | 3.85 |
| 2 | 58 | 50 | 75 | ◎ | ○ | ◎ | >120 | 3.17 |
| 3 | 57 | 48 | 73 | ◎ | ◎ | ◎ | >120 | 3.15 |
| 4 | 59 | 52 | 75 | Δ | ○ | ○ | >120 | 1.82 |

TABLE 2-continued

| | Conditions for forming capsule*1 | | | Performance of capsule | | | | |
| --- | --- | --- | --- | --- | --- | --- | --- | --- |
| | | Temperature of | Temperature of | Shape of capsule*2 | | | Disintegration time (min) | |
| | Gelation | aqueous | | | Gelation | Elasticity of | | |
| Example | temperature (° C.) | composition (° C.) | mold pin (° C.) | Transparency | force | film | pH 1.2 | pH 6.8 |
| 5 | 55 | 45 | 75 | ○ | ◎ | Δ | >120 | 3.52 |
| 6 | 57.5 | 49.5 | 75 | ○ | ◎ | ○ | >120 | 4.03 |
| 7 | 57 | 49 | 73 | ○ | ◎ | ◎ | >120 | 3.81 |
| 8 | 56 | 46 | 75 | Δ | ◎ | ◎ | >120 | 3.38 |
| 9 | 44 | 40 | 75 | Δ | ◎ | ○ | >120 | 4.04 |
| 10 | 57 | 48 | 73 | ◎ | ◎ | ◎ | >120 | 4.96 |
| 11 | 51 | 43 | 73 | ◎ | ◎ | ◎ | >120 | 4.43 |
| 12 | 48 | 40 | 62 | ○ | ◎ | ◎ | >120 | 2.01 |
| 13 | 55 | 47 | 75 | Δ | ○ | ○ | >120 | 3.30 |
| 14 | 61 | 53 | 73 | ○ | ○ | ○ | >120 | 3.70 |
| 15 | 57 | 47 | 73 | ◎ | ◎ | ◎ | >120 | 4.20 |
| 16 | 57 | 48 | 73 | ○ | ◎ | ◎ | >120 | 3.50 |

*1: The method of preparing the capsules according to Examples 1 to 16 is a Hot-pin Process, as a thermal gelation.
*2: The appearance of the capsules was evaluated according to the following standards, and the disintegration was performed based on Korean pharmacopoeia IX disintegration test.

Transparency of Capsules

The dried capsules were transilluminated using a fluorescent lamp, and turbidity of the capsules was observed by visual inspection and gauged into four categories as described below.

◎: clear

○: slightly unclear (slightly rough surface of the capsule or existence of undissolved impurities)

Δ: hazy

×: seriously rough surface or opaque

Gelation Force

The time when the mold pin was taken out of the aqueous composition and placed under room temperature (t=0), and the time (t=t) when the coated aqueous composition started to flow were measured and gauged into four categories as described below.

◎: The aqueous composition does not flow for 60 seconds.

○: The aqueous composition started to flow between 30 to 60 seconds.

Δ: The aqueous composition started to flow between 20 to 30 seconds.

×: The aqueous composition started to flow within 20 seconds.

Elasticity 10 dried capsules were strongly pressed 5 times by hand, and then the number of cracked capsules was measured and gauged into four categories as described below.

◎: 0 to 2

○: 3 to 5

Δ: 5 to 7

Δ: greater than 7

Referring to Table 2, the capsules prepared according to Examples 1 to 16 did not disintegrate for minimum 2 hours in the gastric juice condition, but disintegrate within 5 minutes in the small intestinal juice condition. Thus, it was identified that the capsules have enteric properties. In addition, the capsules had good shapes.

Comparative Examples 1 to 2 and Reference Example 1

Aqueous compositions having compositions listed in Table 3 below were prepared according to the following method, and enteric capsules were prepared in the conditions listed in Table 4 below. Then, each of the prepared capsules was immersed in a test solution having the pH of 1.2 that is similar to gastric juice for maximum 2 hours to observe whether it disintegrate or not, and then immersed in a test solution having the pH of 6.8 that is similar to small intestinal juice to measure disintegration time.

The results are shown in Table 4 below.

Preparation of Aqueous Composition

The components listed in Table 3 below were mixed in water to prepare aqueous compositions or try to prepare aqueous compositions.

Preparation of Enteric Capsule

The temperature of each of the aqueous compositions prepared as described above was controlled to 60° C. Then, a mold pin (Technophar Equipment & Service Ltd, pin, #0) cooled to 25° C. was immersed in the corresponding aqueous composition to coat the aqueous compositions on the mold pin. Then, the coated aqueous composition was gelated. Then, the mold pin coated with the aqueous composition was dried at a temperature ranging from 20 to 40° C. for 30 to 60 minutes.

TABLE 3

| | Composition of aqueous composition (wt %) | | | | | | | |
| --- | --- | --- | --- | --- | --- | --- | --- | --- |
| | Enteric base | Capsule forming aid | Gelating agent | Neutralizing agent | Emulsifier | Plasticizer | | Others |
| | material HPMCP | HPMC 2906 | Agar | NH$_4$OH | SLS | TEC | Glycerin | Ca stearate |
| Comparative Example 1 | 17.43 | — | 0.87 | 2.27 | 0.02 | 0.02 | — | — |

TABLE 3-continued

| | Composition of aqueous composition (wt %) | | | | | | | |
|---|---|---|---|---|---|---|---|---|
| | Enteric base | Capsule forming aid | Gelating | Neutralizing | | Plasticizer | | Others |
| | material HPMCP | HPMC 2906 | agent Agar | agent NH$_4$OH | Emulsifier SLS | TEC | Glycerin | Ca stearate |
| Comparative Example 2 | 73.9 | 9.2 | — | — | — | — | 5.3 | 2.5 |
| Reference Example 1 | 15.6 | 15.6 | — | 1.2 | — | — | — | — |

TABLE 4

| | Conditions for forming capsule | | | Performance of capsule | | | | |
|---|---|---|---|---|---|---|---|---|
| | Gelation temperature (° C.) | Temperature of aqueous composition (° C.) | Temperature of mold pin (° C.) | Shape of capsule | | | Disintegration time (min) | |
| | | | | Transparency | Gelation force | Elasticity of film | pH 1.2 | pH 6.8 |
| Comparative Example 1 | 30 | 60 | 25 | ○ | ○ | ○ | 120 | 25 |
| Comparative Example 2 | Impossible to prepare aqueous composition since components are not completely dissolved in water | | | | | | | |
| Reference Example 1 | — | 60 | 25 | Impossible to prepare a capsule due to insufficient gelating force | | | | |

Referring to Table 4, the capsule prepared using a gelating agent instead of the capsule forming aid according to Comparative Example 1 (Japanese Patent Publication No. 2006-16372 (Qualicaps, Inc.)) was disintegrated in the gastric juice condition within 2 hours and disintegrated in the small intestinal juice condition within 25 minutes. Thus, the capsule prepared in Comparative Example 1 did not have enteric properties. In addition, according to Comparative Example 2 in which a neutralizing agent was not used, it was impossible to prepare an aqueous composition. Comparative Example 2 was in accordance with a method disclosed in U.S. Pat. No. 4,655,840 (Warner-Lambert Company), the method trying to prepare capsules by injection molding using not dissolved enteric base material but melted one. In addition, according to Reference Example 1 in which an aqueous composition was prepared using an enteric base material, a capsule forming aid, and a neutralizing agent, and then a capsule was tried to prepare using freeze-gelation instead of thermal gelation, it was impossible to prepare a capsule since gelation force was not sufficient.

According to an embodiment of the present invention, an enteric hard capsule with excellent quality may be prepared using the aqueous composition including the enteric base material, the capsule forming aid, and the neutralizing agent and gelating features of the enteric base material. The enteric hard capsule has functions that are the same as those of a conventional hard capsule. The enteric hard capsule is not disintegrated and dissoluted in the gastric juice condition (about pH 1.2) for 2 to 4 hours, but is rapidly disintegrated and dissoluted in the small intestinal juice condition (about pH 6.8) within 10 minutes. In addition, since the enteric hard capsule may be prepared using conventional equipment and the aqueous composition has physical properties that may be directly applied to the production of the enteric hard capsule, the enteric hard capsule can be commercially manufactured.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of preparing an enteric hard capsule, the method comprising:
    preparing an aqueous composition by dissolving an enteric base material, a capsule forming aid, and a neutralizing agent in water and maturing the aqueous composition at room temperature;
    preheating the aqueous composition to a first temperature that is less than a gelation temperature for the aqueous composition;
    immersing a mold pin heated to a second temperature that is greater than the gelation temperature for the aqueous composition into the aqueous composition;
    taking the mold pin out of the aqueous composition to obtain a film formed on the mold pin; and
    preparing a capsule shell by maintaining the film at a third temperature that is equal to or greater than the gelation temperature for the aqueous composition for a first time period to fix the film on the mold pin and drying the film at a fourth temperature for a second time period,
    wherein the enteric base material is selected from the group consisting of hydroxypropyl methylcellulose phthalate (HPMCP) and hydroxypropyl methylcellulose acetate succinate (HPMCAS),
    wherein the capsule forming aid is cellulose ether selected from the group consisting of hydroxypropyl methylcellulose (HPMC) and methylcellulose (MC),
    wherein the neutralizing agent is a basic compound, wherein an amount of the neutralizing agent is in a range of 1 to 5% based on a total weight of the aqueous composition; and wherein an amount of the enteric base material is in a range of about 8 to about 25% based on the total weight of the aqueous composition, an amount of the capsule forming aid is in a range of about 1 to about 12% based on the total weight of the aqueous composition; wherein the first temperature is less than the gelation temperature for the aqueous composition by about 4 to about 12.0° C.; wherein the second temperature is greater than the gelation temperature for the aqueous composition by about 10 to about 31° C.;

wherein the third temperature is in a range of about 60 to about 80° C., and the first time period is in a range of about 1 to about 15 minutes; wherein the fourth temperature is in a range of about 20 to about 40° C., and the second time period is in a range of about 30 to about 60 minutes.

* * * * *